United States Patent
Torres-Cardona et al.

(10) Patent No.: US 7,291,749 B2
(45) Date of Patent: Nov. 6, 2007

(54) METHOD FOR PRODUCING ESTERIFIED ASTAXANTHIN FROM ESTERIFIED ZEAXANTHIN

(75) Inventors: Mario D. Torres-Cardona, Nuevo Leon (MX); Gustavo Rodriquez, Sinaloa (MX); George C. Schloemer, Longmont, CO (US)

(73) Assignee: DSM IP Assets B.V., Te Heerlen (NL)

( * ) Notice: Subject to any disclaimer, the term of this patent is extended or adjusted under 35 U.S.C. 154(b) by 315 days.

(21) Appl. No.: 10/685,194

(22) Filed: Oct. 14, 2003

(65) Prior Publication Data
US 2004/0158097 A1    Aug. 12, 2004

Related U.S. Application Data

(60) Provisional application No. 60/421,623, filed on Oct. 25, 2002.

(51) Int. Cl.
*C07C 67/02* (2006.01)
(52) U.S. Cl. ...................................................... 560/259
(58) Field of Classification Search ................. 560/259
See application file for complete search history.

(56) References Cited

U.S. PATENT DOCUMENTS 4,105,855 A    8/1978   Schulz et al.
5,959,138 A *  9/1999   Torres-Cardona et al. .. 560/190
6,372,946 B1   4/2002   Schloemer et al.
6,376,717 B2   4/2002   Schloemer et al.

FOREIGN PATENT DOCUMENTS

| JP | 11290094 A2 | 10/1999 |
| WO | WO 00/62625 | 10/2000 |
| WO | 03/003848 | 1/2003 |
| WO | WO 03/066583 | 8/2003 |

OTHER PUBLICATIONS

Von FRank Kleazie et al , Helvetica chimica Act., vol. 61, Fasc 7, 1978, p. 2609-2615.*
International Search Report mailed May 17, 2004, in a related, pending foreign application.

* cited by examiner

*Primary Examiner*—Taylor Victor Oh
(74) *Attorney, Agent, or Firm*—Nixon & Vanderhye PC

(57) ABSTRACT

A method is described for preparing astaxanthin esters from zeaxanthin by acylation of zeaxanthin with an acylating agent followed by contacting the esterified zeaxanthin with an oxidizing agent to produce esterified astaxanthin. The astaxanthin esters are more stable and show a better bioavailability than free astaxanthin when used in salmonid pigmentation.

20 Claims, No Drawings

METHOD FOR PRODUCING ESTERIFIED ASTAXANTHIN FROM ESTERIFIED ZEAXANTHIN

RELATED APPLICATIONS

This application claims priority to U.S. provisional application No. 60/421,623, filed Oct. 25, 2002, which is incorporated herein by reference in its entirety.

BACKGROUND OF THE INVENTION

1. Field of the Invention

In one embodiment, the invention relates to a process for preparing esterified astaxanthin. In a preferred embodiment, the conversion of zeaxanthin esters to esterified astaxanthin is described.

2. Description of the Related Art

Salmonids are attractive due to their characteristic pinkish color of the flesh. In the wild this color comes from the oxygenated carotenoids, mainly astaxanthin, found in organisms that make up their diets. When these fishes are cultivated astaxanthin must be included in their feed. Most of the astaxanthin used by the fish culture industry is produced synthetically by Hoffmann La Roche and BASF. This product is free astaxanthin as a racemic optically inactive mixture of the three isomers (3R, 3'R), (3R, 3'S) and (3S, 3'S).

This carotenoid is very unstable and easily degrades when exposed to air, heat or light needing special protection, handling and storage conditions to avoid oxidation.

Another source of free astaxanthin is produced by fermentation from *Phaffia rhodozyma* yeast. Esterified astaxanthin is obtained from algal culture of *Haematococcus pluvialis*. The production of astaxanthin from yeast or algae has not competed successfully with the synthetic product.

The production of free astaxanthin derived from the pigment of marigold flowers is described in U.S. Pat. Nos. 6,372,946 and 6,376,717 both assigned to PRODEMEX and incorporated herein by reference.

In salmonids, the oxycarotenoids are deposited in the flesh in the free form, while in skin, predominantly esters are found. In nature astaxanthin is often present as diester.

Usually the esterified carotenoids are more soluble in lipids than the free carotenoids and this represents an advantage as they can easily be incorporated in the feeds.

Previously Torres-Cardona has discussed the fact that esterified carotenoids like lutein and zeaxanthin show better stability and bioavailability than their free forms when used as pigmenters in poultry and aquaculture and also a process is mentioned for esterification in an aqueous medium. Breivik (WO 00/62625 and WO 03/003848) demonstrated that when free astaxanthin was esterified with short chain omega-3 fatty acids a more stable and efficient carotenoid was obtained for salmonid pigmentation.

Tanaka (JP11290094) reported a process for esterification of astaxanthin with linear or branched carboxylic acids of 14 to 22 carbons using one or several types of lipases for synthesis. Then Anderson describes a general procedure for esterification of astaxanthin using a dehydrating agent which later Gloor (WO 03/066583) adapts to implement a process of industrial interest using the synthetic astaxanthin produced by Hoffmann-LaRoche as a starting material.

An embodiment of the invention describes a method for the production of esterified astaxanthin using zeaxanthin esters as starting material.

SUMMARY OF THE INVENTION

In one embodiment, the present invention is directed to a method of preparing esterified astaxanthin from zeaxanthin which includes the steps of acylating zeaxanthin in an organic solvent with an acylating agent to produce esterified zeaxanthin; and contacting the esterified zeaxanthin with an oxidizing agent to produce esterified astaxanthin. In a preferred embodiment, the organic solvent is either chloroform or methylene chloride. Preferably, the ratio of the organic solvent to the zeaxanthin esters is between 5 to 40 parts for each one.

The acylating agent may be RCOOH, RCOCl or $(RCO)_2O$, where R is a hydrocarbon chain of 2-20 hydrocarbons. In a preferred embodiment, R is a hydrocarbon chain of 2-8 hydrocarbons. More preferably, R is a hydrocarbon chain of 2-4 hydrocarbons. In a preferred embodiment, the acylating agent is acetic anhydride.

In a preferred embodiment, the oxidizing agent is produced by mixing a saturated aqueous solution which is any of sodium sulfite, potassium sulfite, sodium hydrogen sulfite, potassium hydrogen sulfite, sodium bisulfite or potassium bisulfite, with a saturated solution of a bromate salt. In a preferred embodiment, the oxidizing agent is produced by mixing a saturated aqueous solution of sodium bisulfite with a saturated solution of sodium bromate. Preferably, the ratio of sodium bisulfite to the sodium bromate is about 1.5:1.

In another preferred embodiment, the oxidizing agent is produced by mixing a saturated aqueous solution of sodium bisulfite with a saturated solution of potassium bromate. In another preferred embodiment, the oxidizing agent is produced by mixing a saturated aqueous solution of sodium bisulfite with a saturated solution of calcium bromate. In another preferred embodiment, the oxidizing agent is produced by mixing a saturated aqueous solution of sodium bisulfite with a saturated solution of cerium bromate. Preferably, the ratio of the oxidizing agent to the zeaxanthin esters is between 0.5 to 5 parts for each part of carotenoid. Preferably, the pH of the aqueous oxidizing agent is between 1 to 4. Preferably, the reaction temperature is between 0 to 25° C.

Preferably, the zeaxanthin is obtained by saponification of a plant extract. More preferably, the plant is marigold. In an alternate preferred embodiment, the zeaxanthin is prepared synthetically.

In some embodiments of the invention, the method includes the step of washing the esterified zeaxanthin with water before contacting the esterified zeaxanthin with the oxidizing agent.

In another aspect, the invention is directed to an astaxanthin diester produced by the method described herein. Preferably, the astaxanthin diester is an astaxanthin diacetate.

Further aspects, features and advantages of this invention will become apparent from the detailed description of the preferred embodiments which follow.

DETAILED DESCRIPTION OF THE PREFERRED EMBODIMENT

The starting material may be a marigold extract with a high concentration of carotenoids in the range of 500 to 1000 g of xanthophylls/Kg of concentrate of which 70 to 100% may be zeaxanthin and the rest mainly lutein and other pigments. Other natural sources may be used to provide zeaxanthin as the starting material.

Alternatively, zeaxanthin may be prepared synthetically. A method for providing zeaxanthin in good yield from lutein is described in U.S. Pat. No. 5,973,211 which is incorporated herein by reference.

The concentrate is mixed with about two to six times, preferably about three times a chlorinated solvent such as chloroform or methylene chloride and about 0.4 to 2 times, preferably about 0.5-1 times acetic anhydride or other acylating agent on a weight: volume basis. Preferably, the acylating agent is an acid anhydride, acid chloride or a carboxylic acid. The choice of acylating agent depends upon the desired length of the carbon chain in the ester portion of the final astaxanthin product. Zeaxanthin is preferably acylated with a carbon chain of $C_2$ to $C_{20}$ length, more preferably the length is $C_2$ to $C_8$ and most preferably the length of the carbon chain is $C_2$ to $C_5$. The carbon chain may be saturated or unsaturated and may include branched or cyclic compounds. In a preferred embodiment, the acetate diesters are prepared using acetic anhydride as the acetylating agent. In a preferred embodiment, three carbon diesters are prepared using propionic anhydride as the acylating agent. In a preferred embodiment, four carbon diesters are prepared using butyric anhydride as the acylating agent and in still another preferred embodiment five carbon diesters are prepared using caproic anhydride.

The mixture is refluxed for a period of about 1-6 hours, preferably, 2 to 4 hr or until at least about 50%, preferably at least about 75% of the pigments have been acylated. In a preferred embodiment, this material is then washed with water to eliminate the residual acid. The washed product is then dissolved in about an additional five to fifty parts, preferably six to ten parts, and more preferably about seven to eight parts, of chlorinated solvent such as chloroform or methylene chloride at about 15-40° C., preferably, about 25° C. Preferably, the washed product is dissolved with vigorous agitation in a sealed reaction vessel.

In one embodiment, the invention is directed to a method of treating esterified zeaxanthin with oxidizing agents. Non-limiting examples of performing allylic oxidations or agents that may be employed in oxidation reactions have been reviewed in the major reference books by Trost and Larock, "*Comprehensive Organic Synthesis*," Volume 7, Pergamon Press, New York, 1991, pages 83-117, and Richard C. Larock "*Comprehensive Organic Transformations*," Wiley-VCH, New York, 1999, pages 1207-1209, which are incorporated herein in their entirety by reference.

In one embodiment, the oxidizing agent is formed by mixing an acidified aqueous solution of a salt of sulfite, hydrogen sulfite or bisulfite with a bromate salt in water. In a preferred embodiment, a saturated aqueous solution of sodium bisulfite is reacted with a saturated solution of sodium bromate in a ratio of about 1-3:1, preferably about 1.0 to 1.5:1 with moderate mixing. Preferably, the reaction is carried out in the dark and at a temperature between 0 to 25° C., preferably between 0 to 10° C. in a separate vessel. The oxidant formed corresponds to about two to four equivalents to one of carotenoids in the mix. The oxidant is added to the reactor containing the esterified zeaxanthin while adjusting the temperature between about 0 to 40° C. but preferably between about 10 to 20° C. The reaction is then carried out with mixing. Preferably, the reaction is carried out with mixing at 400 to 800 rpm in the dark. The reaction will take place in 1 to 60 minutes but usually between 15 to 30 minutes or may be stopped when no zeaxanthin esters are detected in the reaction mixture. The reaction may be stopped by using a sodium carbonate or sodium sulfite saturated aqueous solution and an antioxidant like alpha tocopherol, ascorbyl palmitate, BHA, BHT, ethoxiquin, TBHQ, propyl gallate, etc. The product may yield 30 to 80% of carotenoids in the starting material of which 70 to 90% is esterified astaxanthin.

EXAMPLES

Example 1

The starting material was a marigold extract with a high concentration of carotenoids in the range of 650 to 750 g of carotenoid/kilogram of concentrate of which 70 to 95% were zeaxanthin and the rest mainly lutein and other pigments. The concentrate was mixed with about three times chloroform and 0.5 times acetic anhydride on a weight to volume basis. The mixture was refluxed for a period of 4 to 5 hours or until at least 75% of the pigments had been acetylated. This material was then washed with water to eliminate the residual acetic acid. The washed product was then dissolved in about an additional seven to eight parts of chloroform at about 25° C. with vigorous agitation in a sealed reaction vessel. In a separate vessel, a saturated aqueous solution of sodium bisulfite was reacted with a saturated solution of sodium bromate in a 1.5 to 1 ratio with moderate mixing, in the dark and at a temperature between 0 to 10° C. The oxidant formed corresponded to about two to four equivalents to one of carotenoids in the mix. The oxidant was added to the reactor while adjusting the temperature between 10 to 20° C. The reaction was then carried out with vigorous mixing in the dark. The reaction was stopped when no zeaxanthin esters were detected in the reaction mixture. The product yielded 30 to 80% of the carotenoids in the starting material of which 70 to 90% were esterified astaxanthin.

Example 2

In a sealed reaction vessel, 25 gr. of carotenoids were placed and dispersed in 5 parts of chloroform at room temperature. The carotenoids were comprised of 90% zeaxanthin obtained from marigold flowers. Then 2 parts of acetic anhydride were added and the temperature was raised to reflux. A constant and intense agitation was maintained until no free zeaxanthin was detected by TLC. This process took about 4 hours. The reaction mixture was then washed two times in ten parts of water to remove the residual acetic acid. An additional five parts of chloroform were added and the temperature was adjusted to 20° C. while mixing.

In a separate vessel, a saturated solution of sodium bromate (one part) was mixed with sodium bisulfite (one part) to obtain the oxidant. The temperature of this mixture was also adjusted to 20° C.

The oxidant was added to the reaction vessel with the zeaxanthin esters in a time span of 15 minutes and the reaction was carried out until no zeaxanthin esters were detected. At this point, 2 parts of a saturated solution of sodium carbonate was added and mixing was continued for 10 minutes. Next, two washes with 10 volumes of water each were performed. In each, the aqueous phase was separated and eliminated. The solvent was removed under reduced pressure and 15 gr. of astaxanthin esters were obtained which represents about a 60% yield.

Example 3

In a glass reactor, 45 gr. of marigold zeaxanthin esters with 92% purity were used as starting material. To these, 15 parts of methylene chloride were added and the temperature was adjusted to 0° C. The reactor remained sealed with vigorous mixing.

In another vessel, the oxidation solution was prepared by mixing saturated solutions of 4 equivalents of calcium bromate in relation to the initial carotenoids and one equivalent of sodium bisulfite in relation to the bromate used. The temperature was adjusted to 0° C. and the pH to 3 using a dilute solution of hydrobromic acid.

The oxidant was added slowly during two hours and the reaction was continued until there was no presence of zeaxanthin esters which usually takes around six hours.

After reaction, three parts of a saturated solution of sodium sulfite were added and mixed for 10 minutes and the 0.1 gr. of ethoxyquin plus 0.1 gr. of ascorbyl palmitate were added and mixed for another 10 minutes.

The mixture was allowed to rest and the water phase removed followed by two washings with 10 volumes of water each. The solvent was then removed and 19 gr. of astaxanthin esters were obtained representing about 40% yield.

Example 4

In 40 parts of chloroform (V/W), 30 gr. of zeaxanthin esters were dispersed at room temperature. The reactor was sealed while adjusting the temperature to 10° C. and mixing was set to about 800 rpm.

In a separate vessel the oxidizing solution was prepared using six equivalents of cerium bromate in relation to the initial carotenoids and two equivalents of sodium bisulfite relative to the bromate used. Both solutions were saturated and aqueous. The temperature of the mixture was adjusted to 10° C. and the pH to 2.5 using a dilute solution of sulfuric acid.

The oxidant was added all at once to the reactor keeping the same temperature and the reaction was stopped when no zeaxanthin was detected which was at about 20 minutes. To stop the reaction, one part of a saturated solution of sodium carbonate was added along with one part of a saturated solution of sodium sulfite plus 0.2 gr. ethoxyquin. After mixing for 10 minutes, the aqueous phase was separated and two washings were given to the organic phase as described in example 3.

After solvent elimination, 30 gr. of astaxanthin esters were obtained representing a 70% yield.

Example 5

In a glass reactor, 50 gr. of a zeaxanthin concentrate from marigold, prepared following the method described in U.S. Pat. No. 5,973,211, were dispersed in 4 volumes of chloroform (V/W) with continuous mixing. The concentrate had 95% xanthophylls of which 90% was zeaxanthin and the rest mainly lutein. Once a homogeneous suspension has been formed with the concentrate, 20 gr. of acetic anhydride were added. The reactor was then sealed and the temperature raised to obtain a moderate reflux. After 4 hours of reaction, TLC indicated the presence of mainly esters of zeaxanthin and low amount of lutein esters. More than 80% of the esters were in the diacetate form and the rest as monoacetate. A couple of washings with ten parts of water were performed at ambient temperature. The yield of reaction was 95%. Ten additional parts of chloroform were added to the residual organic phase and mixed until homogeneous. In a small volume of water (30 ml), 250 mg of sodium iodide were dissolved and added to the mixture. Also in a small volume of solvent, 250 mg of metallic iodine were dissolved and added to the mixture. The reactor was then sealed and the temperature adjusted to about 2° C., while maintaining vigorous stirring at about 1000 rpm.

In another vessel the oxidant is prepared by mixing five equivalents of a saturated solution of sodium bromate in respect to the total carotenoids with a saturated solution of sodium metabisulfite using 0.5 parts to 1 (V/W) relative to the sodium bromate. The temperature of the oxidizing mixture was kept between 0 to 10° C. The oxidant was then added to the suspensions of zeaxanthin esters in four hours and the reaction was continued. This usually takes about 6 hours.

After reaction, 2 parts of a saturated solution of sodium sulfite were added along with 100 mg of propylgallate and 50 mg of ascorbyl palmitate and mixed for 10 minutes at room temperature. The aqueous phase was separated and the organic phase was washed three times with 10 parts of water each. The solvent was eliminated and 35 gr. of astaxanthin esters were obtained of which 70% were diesters and the rest monoesters. The global yield was about 70%.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of preparing esterified astaxanthin from zeaxanthin comprising the steps of:
   acylating zeaxanthin in an organic solvent with an acylating agent to produce esterified zeaxanthin; and
   contacting the esterified zeaxanthin with an oxidizing agent to produce esterified astaxanthin.

2. The method of claim 1, wherein the organic solvent is selected from the group consisting of chloroform and methylene chloride.

3. The method of claim 1, wherein the acylating agent is selected from the group consisting of RCOOH, RCOCl and $(RCO)_2O$, wherein R is a hydrocarbon chain of 2-20 hydrocarbons.

4. The method of claim 3, wherein R is a hydrocarbon chain of 2-8 hydrocarbons.

5. The method of claim 3, wherein R is a hydrocarbon chain of 2-4 hydrocarbons.

6. The method of claim 3, wherein the acylating agent is acetic anhydride.

7. The method of claim 1, wherein the oxidizing agent is produced by mixing a saturated aqueous solution selected from the group consisting of sodium sulfite, potassium sulfite, sodium hydrogen sulfite, potassium hydrogen sulfite, sodium bisulfite and potassium bisulfite, with a saturated solution of a bromate salt.

8. The method of claim 7, wherein the oxidizing agent is produced by mixing a saturated aqueous solution of sodium bisulfite with a saturated solution of sodium bromate.

9. The method of claim 8, wherein the ratio of sodium bisulfite to sodium bromate is about 1.5:1.

10. The method of claim 7, wherein the oxidizing agent is produced by mixing a saturated aqueous solution of sodium bisulfite with a saturated solution of potassium bromate.

11. The method of claim 7, wherein the oxidizing agent is produced by mixing a saturated aqueous solution of sodium bisulfite with a saturated solution of calcium bromate.

12. The method of claim 7, wherein the oxidizing agent is produced by mixing a saturated aqueous solution of sodium bisulfite with a saturated solution of cerium bromate.

13. The method of claim 1, which is practiced at a reaction temperature between 0 to 25° C.

14. The method of claim 7, wherein the oxidizing agent and the zeaxanthin esters are present in a ratio of the oxidizing agent to the zeaxanthin esters of between 0.5 to 5 parts for each part of carotenoid.

15. The method of claim 7, wherein the aqueous oxidizing agent has a pH of between 1 to 4.

16. The method of claim 2, wherein the organic solvent and zeaxanthin esters are present in a ratio of the organic solvent to the zeaxanthin esters of between 5 to 40 parts for each one.

17. The method of claim 1, wherein the zeaxanthin is obtained by saponification of a plant extract.

18. The method of claim 17, wherein the plant is marigold.

19. The method of claim 1, wherein the zeaxanthin is prepared synthetically.

20. The method of claim 1, further comprising the step of washing the esterified zeaxanthin with water before contacting the esterified zeaxanthin with the oxidizing agent.

* * * * *